(12) United States Patent
Halling et al.

(10) Patent No.: US 8,517,022 B2
(45) Date of Patent: Aug. 27, 2013

(54) MINIMALLY INVASIVE NASAL CANNULA

(75) Inventors: Jordan Halling, Riverton, UT (US); Brian Halling, Riverton, UT (US)

(73) Assignee: JBR Holding, L.C., Holladay, UT (US)

( * ) Notice: Subject to any disclaimer, the term of this patent is extended or adjusted under 35 U.S.C. 154(b) by 1058 days.

(21) Appl. No.: 12/229,214

(22) Filed: Aug. 19, 2008

(65) Prior Publication Data

US 2010/0043801 A1     Feb. 25, 2010

(51) Int. Cl.
*A61G 10/00* (2006.01)

(52) U.S. Cl.
USPC ................................. 128/206.11

(58) Field of Classification Search
USPC .......... 128/207.18, 200.24, 200.26, 206.11, 128/207.13, 203.22, 203.23
See application file for complete search history.

(56) References Cited

U.S. PATENT DOCUMENTS

| | | | |
|---|---|---|---|
| 4,273,124 A | 6/1981 | Zimmerman | |
| 4,648,398 A | 3/1987 | Agdanowski et al. | |
| 4,753,233 A * | 6/1988 | Grimes | 128/207.18 |
| 5,099,836 A * | 3/1992 | Rowland et al. | 128/204.23 |
| 5,105,807 A * | 4/1992 | Kahn et al. | 128/207.18 |
| 5,113,857 A | 5/1992 | Dickerman et al. | |
| 5,533,506 A | 7/1996 | Wood | |
| 5,682,881 A | 11/1997 | Winthrop et al. | |
| 6,119,690 A | 9/2000 | Pantaleo | |
| 6,478,026 B1 | 11/2002 | Wood | |
| 6,561,188 B1 * | 5/2003 | Ellis | 128/206.11 |
| 6,805,126 B2 * | 10/2004 | Dutkiewicz | 128/207.18 |
| 6,848,446 B2 | 2/2005 | Noble | |
| 6,913,017 B2 | 7/2005 | Roberts | |
| RE42,843 E * | 10/2011 | Strickland et al. | 128/207.18 |
| 2003/0079749 A1 | 5/2003 | Strickland et al. | |
| 2003/0094178 A1 | 5/2003 | McAuley et al. | |
| 2005/0121037 A1 | 6/2005 | Wood | |
| 2006/0112961 A1 | 6/2006 | Aly | |
| 2007/0107737 A1 * | 5/2007 | Landis et al. | 128/207.18 |
| 2008/0051674 A1 * | 2/2008 | Davenport et al. | 600/561 |
| 2009/0101147 A1 * | 4/2009 | Landis et al. | 128/204.18 |

* cited by examiner

*Primary Examiner* — Elizabeth Houston
*Assistant Examiner* — Bradley Philips
(74) *Attorney, Agent, or Firm* — Paul C. Oestreich; Eminent IP, P.C.

(57) ABSTRACT

A light weight securable nasal cannula and system including the nasal cannula for delivering therapeutic gas, e.g., oxygen, to the nostrils of a patient. The nasal cannula may include a hollow body having at least one inhale aperture defined therein and at least one nasal insert therein. Each nasal insert may include a nasal insert tube associated with the nasal insert of the body. Each nasal insert may further include at least one exhale aperture adjacent to the nasal insert tube, wherein each of the exhale apertures, either alone or in combination, has a cross-sectional area greater than a cross-sectional area of the nasal insert tube. Each nasal insert may further include an annular sleeve surrounding the nasal insert tube and the at least one exhale aperture, the annular sleeve including a contact surface formed thereon and configured for placement against an inside surface of the nostril to achieve a friction fit.

21 Claims, 5 Drawing Sheets

MINIMALLY INVASIVE NASAL CANNULA

BACKGROUND OF THE INVENTION

1. Field of the Invention

This invention relates generally to nasal ventilation systems, and more particularly, to a minimally invasive nasal cannula.

2. Description of Related Art

Conventional nasal ventilators generally consist of tubes and other means for delivering therapeutic gases adapted for use with the nasal or oral passage of a patient. Typically, a nasal ventilation system comprises a gas source and a mechanical ventilator such as a continuous positive airway pressure (CPAP) system, bi-level positive airway pressure (BIPAP) system, or intermittent positive pressure breathing (IPPB) system. The gas may be room air, oxygen-enriched air, or a mixture of other gases, e.g., anesthetic gases.

In such conventional nasal ventilators, the gas is transported by a thin flexible main tube made of an inert material. The main tube terminates at an opening which can be inserted into the patient's nostrils. Typically, a pair of smaller nasal insert tubes protrude from the main tube, or the main tube splits at a Y-junction into two smaller tubes. Each smaller nasal insert tube is generally inserted some distance into a nasal cavity to carry gas to the nostril, thereby increasing the fraction of inspired oxygen.

Additionally, conventional nasal tube systems generally do not provide a positive seal between the nasal insert tubes and the nostrils. Thus, some conventional nasal ventilation systems include a mask that fits over the nose that is intended to provide a space of oxygen-enriched air for inhalation into the lungs for respiration. Such systems frequently suffer from air leaking out around the mask, creating an inability to assure ventilation in many patients.

For example, such conventional nasal ventilation systems use head gear and/or straps to bind the mask in place. But in order to minimize the leakage of the air the straps must be sufficiently tight. The mask, headgear, and/or straps thereby exert uncomfortable pressure on the patient's face and/or head, resulting in such masks and headgear tending to be rather constraining and uncomfortable for the patient.

Additionally, many conventional systems tend to be position dependent, whereby if the mask is moved slightly with respect to the facial contour or with respect to the nose, air leakage occurs. With such systems, the mask can become uncomfortable when not in position, thus requiring the patient to remain stationary in order to alleviate the discomfort and to maintain oxygen inspiration. As a result many patients lose interest in using the nasal mask, defeating the purpose of the ventilation system. Thus, nasal ventilation systems typically rely on a seal between the system and the patient to allow the ventilation system to operate properly.

As an alternative to mask-based ventilation systems, it is known to provide a seal against the inside of a patient's nasal cavity using the nasal cannula itself. For example, U.S. Pat. No. 5,533,506 to Wood discloses a nasal insert having a conical shape and a soft membrane covering the tapered end in conjunction with a washer for sealing against the inside of a patient's nostril. U.S. Pat. No. 6,478,026 also to Wood discloses a nasal cannula having annular sleeves made of a soft pliable material for patient comfort, such as a silicone elastomer, to form a gentle but firm seal with the inner wall of one of the patient's nostrils. U.S. Pat. No. 6,848,446 to Nobel discloses nasal inserts of various pre-configured shapes configured to be self-retaining without the use of straps or ear hooks to hold it in place. Similarly, U.S. Pat. No. 4,648,398 to Agdanowski et al. and U.S. Pat. No. 5,105,807 to Kahn et al. both disclose sponge-like nasal inserts for insertion into the nostrils of a patient that are manually compressible with a relatively slow rate of expansion to achieve a seal with patient nostrils.

U.S. Pat. No. 5,113,857 to Dickerman et al. discloses sealant pads in conjunction with a septum clip for sealing a nasal interface to a patient's nasal openings. The Dickerman et al. sealant pads are formed of a soft resilient material, and are partially inserted into the nostril, but appear to seal, at least partially, against the outer surface of the nasal opening. U.S. Pat. No. 4,753,233 to Grimes discloses nasal cannula with integrated converse excurvated tips that allow the cannula to float in the nares of the patient's nose without a pinch fit like the Dickerman et al. device. Inflatable nasal cannula are disclosed in U.S. Pat. No. 4,273,124 to Zimmerman and U.S. Patent Application Publication No. 2003/0094178 to McAuley et al.

Regarding ventilator systems with seals, various valve systems have been devised to allow a patient to inhale therapeutic gas and also exhale from their lungs. In some conventional ventilation systems, the exhalation valve is positioned at the ventilator or in the tubing some distance from the patient. The air that is exhaled by the patient is trapped in a "dead space" between the patient and the valve. Such ventilation systems with exhale valves tend to be bulky and heavy. Additionally, the patient needs to have a tidal volume (breath) that is a little larger than otherwise needed to compensate for the dead space. This larger tidal volume is noticeable by the patient and can be a nuisance while trying to sleep soundly. To solve this dead space problem, the placement of the exhalation valve in the nasal cannula itself has been proposed, see e.g., U.S. Pat. No. 6,478,026 to Wood.

Other types of conventional nasal tube systems include low flow oxygen systems which merely provide oxygen concentration to the patient. These systems typically provide nasal insert tubes that are loosely inserted into the nasal cavities without a mask or seal. Such systems are low pressure systems for providing oxygen enrichment to the ambient air that the patient breathes, i.e., provide elevated oxygen saturation to the patient. However, such low flow oxygen systems are not ventilators, i.e., they do not provide positive pressure for forced ventilation and/or breathing, and could not function as ventilation systems because of the lack of a seal between the cannula interface and the patient, the smaller tubing size, and the low pressure of the system. Because of the lack of a seal in such low flow oxygen systems, the patient can exhale through nasal passages around the length of tube inserted into the nasal cavity.

The nasal insert tubes of such conventional low flow oxygen systems are generally uncomfortable for the patient because of the length of tube inserted into the nasal cavity. Patients are known to intentionally remove the nasal insert tube because of the discomfort. Additionally, such nasal insert tubes are known to become dislodged from within the nasal passages or "nares" because of patient movement during sleep.

Accordingly, there exists a need in the art for a low flow oxygen system nasal interface apparatus that overcomes at least some of the above-mentioned problems with conventional low flow oxygen system nasal cannula. It would be advantageous to have a nasal cannula that is minimally invasive and generally comfortable for the patient to wear. It would be further advantageous to have a nasal cannula that remains comfortably within a patient's nasal passage. It would be further advantageous to have a nasal cannula that also provides a means for exhaling through the nasal passages as well as for delivering oxygen or other therapeutic gases.

SUMMARY OF THE INVENTION

An embodiment of a nasal cannula according to the present invention is disclosed. The embodiment of a nasal cannula may include a hollow body having at least one inhale aperture defined therein and at least one nasal insert therein. Each nasal insert may include a nasal insert tube associated with the nasal insert of the body, wherein the nasal insert tube is configured to be inserted into a nostril of a patient. Each nasal insert may further include at least one exhale aperture adjacent to the nasal insert tube, wherein each of the exhale apertures, either alone or in combination, has a cross-sectional area greater than a cross-sectional area of the nasal insert tube. Each nasal insert may further include an annular sleeve surrounding the nasal insert tube and the at least one exhale aperture, the annular sleeve including a contact surface formed thereon and configured for placement against an inside surface of the nostril to achieve a friction fit.

An embodiment of a low flow gas system according to the present invention is disclosed. The embodiment of a system may include a nasal cannula. An embodiment of the nasal cannula may include a hollow body having an inhale aperture defined therein and two nasal inserts disposed thereon. Each nasal insert may include a nasal insert tube connected to the hollow body and configured to be inserted into a nostril of a patient. Each nasal insert may further include an exhale aperture adjacent to the nasal insert tube, wherein the exhale aperture has a cross-sectional area greater than a cross-sectional area of the nasal insert tube. Each nasal insert may further include an annular sleeve surrounding the nasal insert tube and the exhale aperture. The embodiment of an annular sleeve may include a contact surface formed thereon and configured for placement against an inside surface of the nostril of the patient to achieve a friction fit. The embodiment of a system may further include a supply tube configured for attachment at one end to the inhale aperture and further configured with a nozzle fitment on an opposite end of the supply tube for attachment to a gas source.

An embodiment of a method for delivering a low flow therapeutic gas to a patient according to the present invention is disclosed. The embodiment of a method may include providing a low flow gas system. The low flow gas system may include a nasal cannula including a hollow body having an inhale aperture defined therein and two nasal inserts disposed thereon. Each embodiment of a nasal insert may include a nasal insert tube associated with the nasal insert of the body, wherein the nasal insert tube is configured to be inserted into a nostril of a patient. Each embodiment of a nasal insert may further include an exhale aperture adjacent to the nasal insert tube, wherein the exhale aperture has a cross-sectional area greater than a cross-sectional area of the nasal insert tube. Each embodiment of a nasal insert may further include an annular sleeve surrounding the nasal insert tube and the exhale aperture, wherein the annular sleeve includes a contact surface formed thereon and configured for placement against an inside surface of the nostril of the patient to achieve a friction fit. The low flow gas system may further include a gas source. The low flow gas system may further include a supply tube configured for attachment at one end to the inhale aperture and configured with a nozzle fitment on an opposite end of the supply tube for attachment to the gas source. The low flow gas system may further include a clip configured for attachment to the supply tube and to patient clothing. The embodiment of a method may further include attaching the nozzle fitment to the gas source. The embodiment of a method may further include inserting the nasal inserts of the nasal cannula into nostrils of the patient. The embodiment of a method may further include setting a gas flow rate of the gas source to a desired level.

Additional features and advantages of the invention will be set forth in the detailed description in conjunction with the drawings of the illustrated embodiments of the invention that follow, and in part will be apparent from the description, or may be learned by the practice of the present invention.

BRIEF DESCRIPTION OF THE DRAWINGS

The following drawings illustrate exemplary embodiments for carrying out the invention. The various features and structural elements of the embodiments of the present invention illustrated in the following drawing FIGS., are not necessarily drawn to scale. Like reference numerals refer to like parts in different views or embodiments of the present invention shown in the drawings.

DETAILED DESCRIPTION

The minimally invasive nasal cannula and system of the present invention is particularly useful in low flow gas systems for delivering therapeutic gases, such as oxygen, to patients. Advantageous features of the nasal cannula and system embodiments of the present invention include increased patient comfort because tubing need not be inserted deep within patient nostrils to hold it in place. Another improved comfort feature is the lack of tubing wrapped around the face or ears of the patient, found in some conventional nasal cannula systems, in order to maintain the tubing within the nostrils. Another advantageous feature is the use of an annular sleeve on each nasal insert to achieve a secure friction fit within the patient's nostril, thereby decreasing occurrences of tubing disengaging from within the patient's nostrils during routine movement or during sleep. Still another advantageous feature is one or more exhale apertures having individual or combined cross-sections that are greater than the cross-section of the nasal insert tube, which delivers therapeutic gas to the patient. Other advantageous features include the nasal cannula's light weight and optional clip for attachment of a supply tube to patient clothing.

Figure 1:
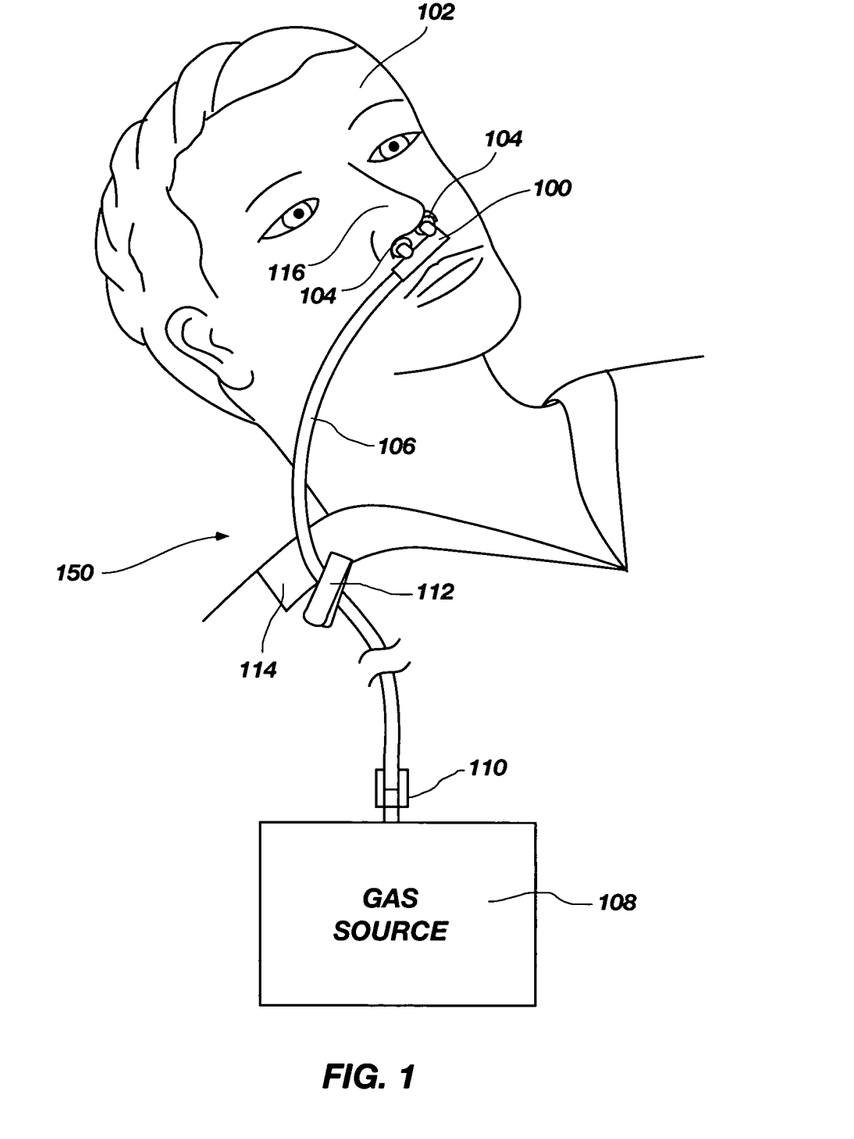
FIG. 1 is a diagram of a patient using an embodiment of the minimally invasive nasal cannula and system according to the present invention.

FIG. 1 is a diagram of a patient 102 using an embodiment of the minimally invasive nasal cannula 100 and system shown generally at arrow 150 according to the present invention. Nasal cannula 100 is shown inserted into the patient's nose 116 at nostrils 104. System 150 may include a nasal cannula 100, attached to a supply tube 106 that leads to a gas source 108. The supply tube 106 may include a nozzle fitment 110 for attachment to the gas source 108, as shown in the illustrated embodiment. According to another embodiment of system 150, the supply tube 106 may be configured to connect to the gas source by other means without a fitment on the supply tube 106 itself as known to those of ordinary skill in the art. For example, the supply tube 106 may attach directly to a fitment or other mechanical means on the gas source 108. The gas source 108 may be an oxygen canister, according to a particular embodiment of system 150. It will be understood that system 150 may be used with other (not oxygen) therapeutic gases and gas sources, according to other embodiments of the present invention. System 150 may further include a clip 112 for attaching the supply tube 106 to an article of clothing 114 (e.g., gown, shirt, etc.) on the patient 102 or other object (not shown) as desired.

Figure 2:
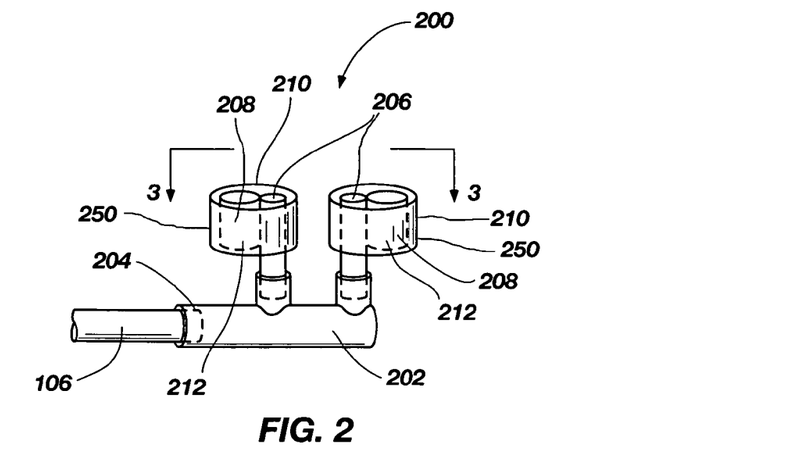
FIG. 2 is a side view of an embodiment of a nasal cannula according to the present invention.

FIG. 2 is a side view of an embodiment of a nasal cannula 200 according to the present invention. Nasal cannula 200 may include a hollow body 202 having at least one inhale aperture 204 (one shown) defined therein. Nasal cannula 200 may further include at least one nasal insert 250 (two shown) defined therein. As noted above, the nasal cannula 200 may include a hollow body 202 including exactly one inhale aperture 204. However, in an alternative embodiment, the hollow body 202 may include a second inhale aperture 204 on an opposite side or other suitable location (not shown).

Each nasal insert 250 may further include a nasal insert tube 206 associated with the nasal insert 250 of the body 202. The nasal insert tube 206 is configured to be inserted into a nostril 104 (FIG. 1) of a patient 102 (FIG. 1). Each nasal insert 250 may further include an exhale aperture 208 adjacent to the nasal insert tube 206.

Figure 3:
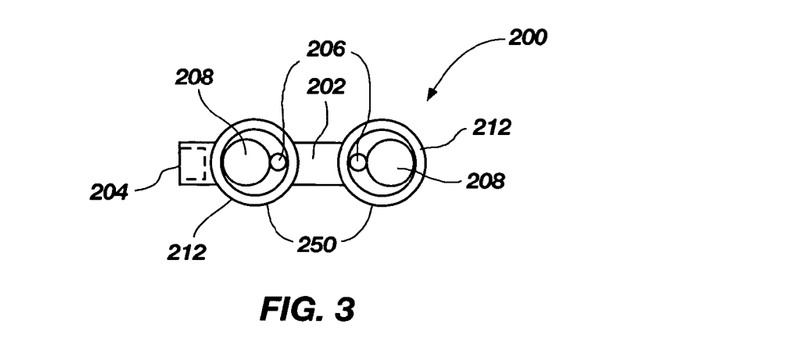
FIG. 3 is a top view of the embodiment of a nasal cannula shown in FIG. 2.

FIG. 3 illustrates a top view of the nasal cannula 200 shown in FIG. 2 with two nasal inserts 250. As shown in FIG. 3, the exhale aperture 208 may be configured with a greater cross-sectional area than the cross-sectional area of the nasal insert tube 206. In other embodiments (see, e.g., FIG. 7 and related discussion below), the exhale aperture 208 may be configured as a plurality of exhale apertures, wherein each of the cross-sectional areas of each exhale aperture (or the combination of cross-sectional areas of each exhale aperture) is greater than the cross-sectional area of the nasal insert tube 206.

Figure 5:
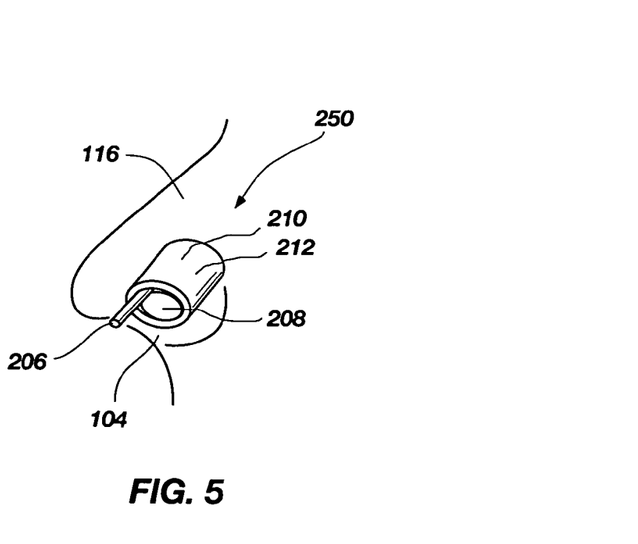
FIG. 5 is a close-up view of an embodiment of a nasal insert inserted into a patient's nostril.

Referring again to FIGS. 2, 3 and 5, each nasal insert 250 may further include an annular sleeve 210 surrounding the nasal insert tube 206 and the exhale aperture 208. The annular sleeve 210 includes a contact surface 212 formed thereon which is configured for placement against an inside surface of the nostril 104 (FIG. 1, see also FIG. 5) to achieve a friction fit. FIG. 5 is a close-up view of a single nasal insert 250 from a nasal cannula 200 (not shown in its entirety) inserted into a patient's nose 116 at nostril 104. According to one embodiment, the annular sleeve 210 may be formed of a resilient elastomer material.

Figure 4:
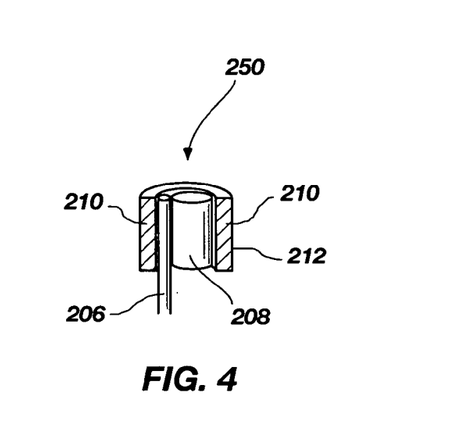
FIG. 4 illustrates a cross-sectional view of an embodiment of a single nasal insert.

FIG. 4 illustrates a cross-sectional view of an embodiment of a single nasal insert 250. The nasal insert 250 includes a nasal insert tube 206 adjacent to an exhale aperture 208. Both the nasal insert tube 206 and exhale aperture 208 are surrounded by an annular sleeve 210. According to a presently preferred embodiment, the annular sleeve 210 may be formed of memory foam padding, i.e., material that may be compressed by rolling or squeezing between fingers and which subsequently expands to its original size or within a smaller volume, such as the inside of a nostril. Thus, an annular sleeve 210 formed of memory foam padding may be compressed before insertion into a patient's nostrils 104 (FIG. 1) and thereby achieve a friction fit upon expansion. Such a friction fit is comfortable for the patient 102 (FIG. 1), and is less likely to cause skin ulceration or breakdown than a conventional cannula with a tube loosely inserted into the nostril and/or nares of a patient 104 (FIG. 1).

Figure 6:
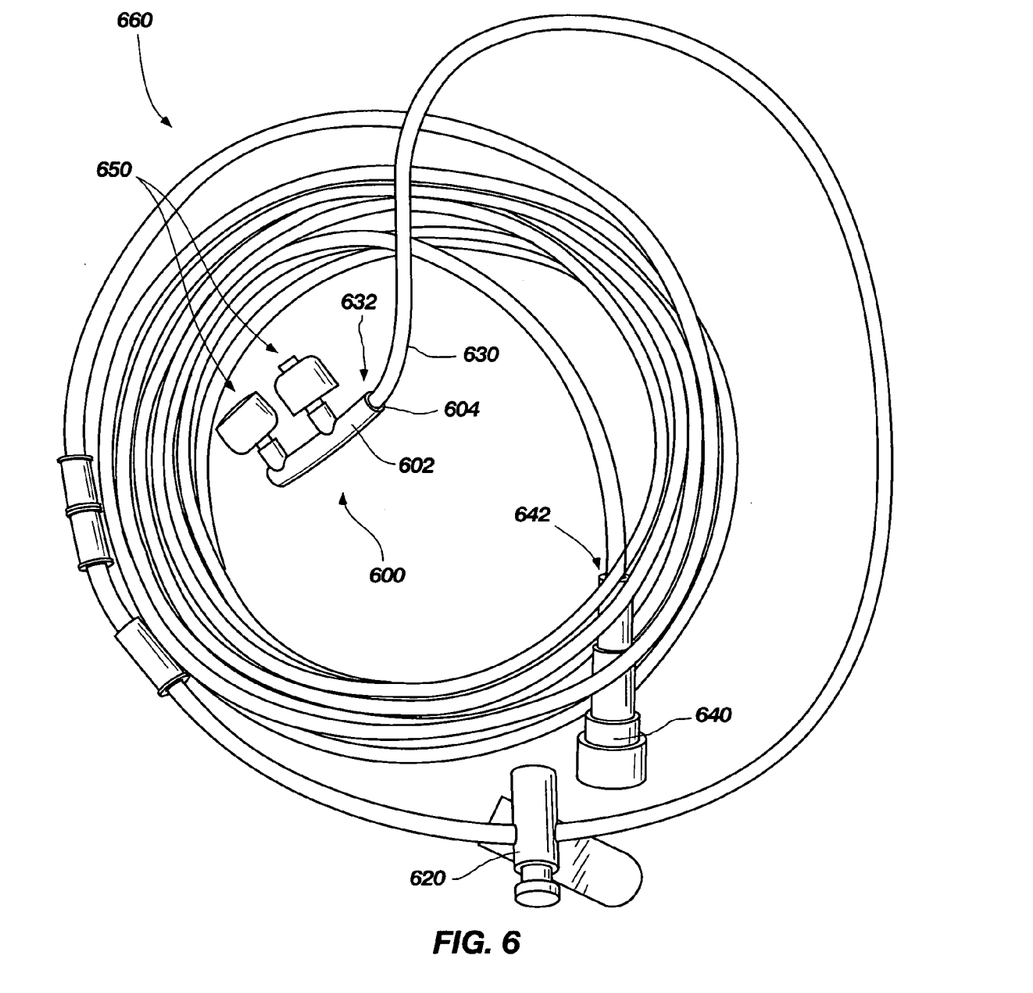
FIG. 6 is an image of an embodiment of a nasal cannula system according to the present invention.

FIG. 6 is an image of an embodiment of a low flow gas system 660 according to the present invention. System 660 may include a nasal cannula shown generally at arrow 600. According to embodiments of the present invention, nasal cannula 600 may have the structural characteristics and features described above with respect to nasal cannula 100 or nasal cannula 200. System 660 may further include a supply tube 630 configured for attachment at one end 632 to the inhale aperture 604 and further configured with a nozzle fitment 640 on an opposite end 642 of the supply tube 630 for attachment to a gas source (not shown in FIG. 6, but see 108 in FIG. 1). System 660 may further include a clip 620 configured for attachment to the supply tube 630 and to patient clothing 114 (FIG. 1).

Figure 7:
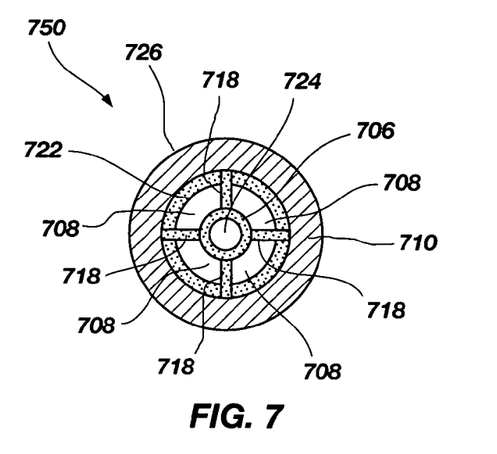
FIG. 7 is a cross-sectional view of another embodiment of a nasal insert according to the present invention.

As shown generally in FIG. 6, nasal cannula 600 may include a hollow body 602 having an inhale aperture 604 and two nasal inserts 650 defined therein). Thus, when system 660 is in use, therapeutic gas (e.g., oxygen) from a gas source (not shown in FIG. 6, but see 108 in FIG. 1) may be delivered through the supply tube 630 to the inhale aperture 604 of the hollow body 602, and into each of the two nasal inserts 650, and into a patient's nostrils 104 (FIGS. 1 and 5). FIG. 7 and the related discussion below expands upon the structural features that may be included in various embodiments of nasal inserts, such as 650 (FIG. 6) and 250 (FIGS. 2-5).

FIG. 7 is a cross-sectional view of another embodiment of a nasal insert 750 according to the present invention. According to this embodiment, nasal insert 750 may include a centrally located nasal insert tube 706 for delivering the therapeutic gas to the patient. Nasal insert 750 further includes four exhale apertures 708 surrounding the nasal insert tube. As shown in the embodiment of FIG. 7, the exhale apertures 708 are defined by radial supports 718, external tube 722 and nasal insert tube 706. While four exhale apertures 708 are shown in FIG. 7, any number of exhale apertures 708 (e.g., one or more) may be defined based on the number or configuration of the radial or other supports, according to other embodiments of the present invention. It will be readily apparent from FIG. 7 that some embodiments of a nasal cannula may include one or more exhale apertures 708 that surround the nasal insert tube 706. According to various embodiments of a nasal cannula, such as a nasal cannula including nasal insert 750, the one or more exhale apertures 708 are defined by radial supports 718 separating the nasal insert tube 706 from an external tube 722 defining an outer circumference of the exhale apertures.

The external tube 722, exhale apertures 708 and nasal insert tube 706 are surrounded by annular sleeve 710. The annular sleeve 710 may be formed of a resilient elastomer or compressible memory foam according to embodiments of the present invention. The external tube 722, exhale apertures 708 and nasal insert tube 706 may be formed of a plastic or other suitable lightweight material that maintains the central aperture 724 of nasal insert tube 706 for delivering a therapeutic gas, and also maintains the exhale apertures 708 for exhaling gas from a patient's lungs (not shown).

According to particular embodiments of a nasal insert 250, 650 and 750 the outer contact surface 212 (FIGS. 2-5 and 726 FIG. 7) of the annular sleeve 710 forms an exclusive contact interface with the nostril. That is to say that the nasal cannulae 100, 200 and 600 disclosed herein may be supported by the friction fit within the patient's nostrils alone, and without the use of headgear, masks or wrapping supply tubing around the ears of the patient common to other conventional cannulae.

Figure 8:
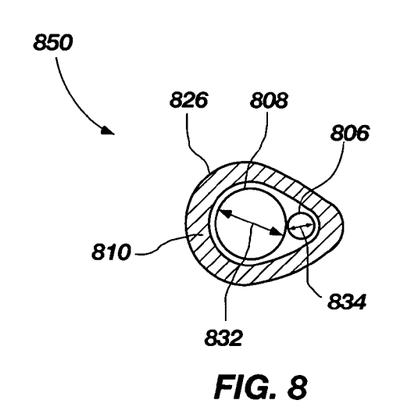
FIG. 8 is a cross-sectional view of yet another embodiment of a nasal insert according to the present invention.

FIG. 8 is a cross-sectional view of yet another embodiment of a nasal insert 850 according to the present invention. Nasal insert 850 includes an exhale tube 808 having exhale aperture diameter 832, a nasal insert tube 806 having inhale aperture diameter 834 and a surrounding annular sleeve 810. As shown in the embodiment of nasal insert 850, the exhale aperture diameter 832 of the exhale tube 808 is greater than the inhale aperture diameter 834 of nasal insert tube 806. This particular configuration and others disclosed herein facilitate patient exhaling through the nostrils in combination with inhalation of therapeutic gases during breathing cycles.

Figure 9:
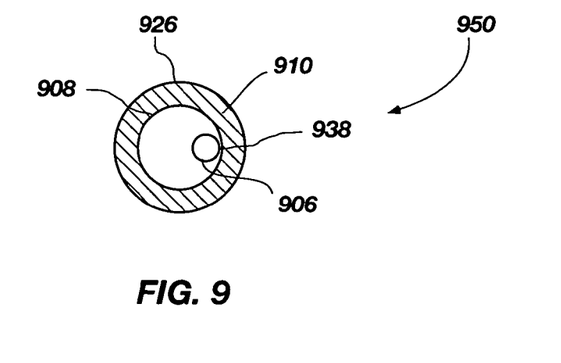
FIG. 9 is a cross-sectional view of still another embodiment of a nasal insert according to the present invention.

FIG. 9 is a cross-sectional view of still another embodiment of a nasal insert 950 according to the present invention. Nasal insert 950 includes an exhale tube 908 having exhale aperture diameter (not illustrated for clarity), a nasal insert tube 906 having inhale aperture diameter (also not illustrated for clarity) and a surrounding annular sleeve 910. As shown in the embodiment of nasal insert 950 of FIG. 9, the nasal insert tube 806 is adjacent to an inside surface 938 of the exhale tube 908.

The outer surface 212, 726, 826 and 926 of annular sleeve 210, 710, 810 and 910, as shown in cross-section in FIGS. 3 and 7-9, may be generally circular (FIGS. 3, 7 and 9), irregular (FIG. 8) or any other suitable shape for engaging the inside of a patient's nostril 104 (FIGS. 1 and 5). For example and not be way of limitation, the outer surface cross-section may be elliptical, oval, or any other suitable shape according to other embodiments. Such other outer surface cross-sectional shapes are known to those skilled in the art, see e.g., U.S. Pat. No. 5,105,807 to Kahn et al., U.S. Pat. No. 4,648,398 to Agdanowski et al. and U.S. Pat. No. 6,848,446 to Noble, all of which are incorporated herein by reference for all purposes.

Figure 10:
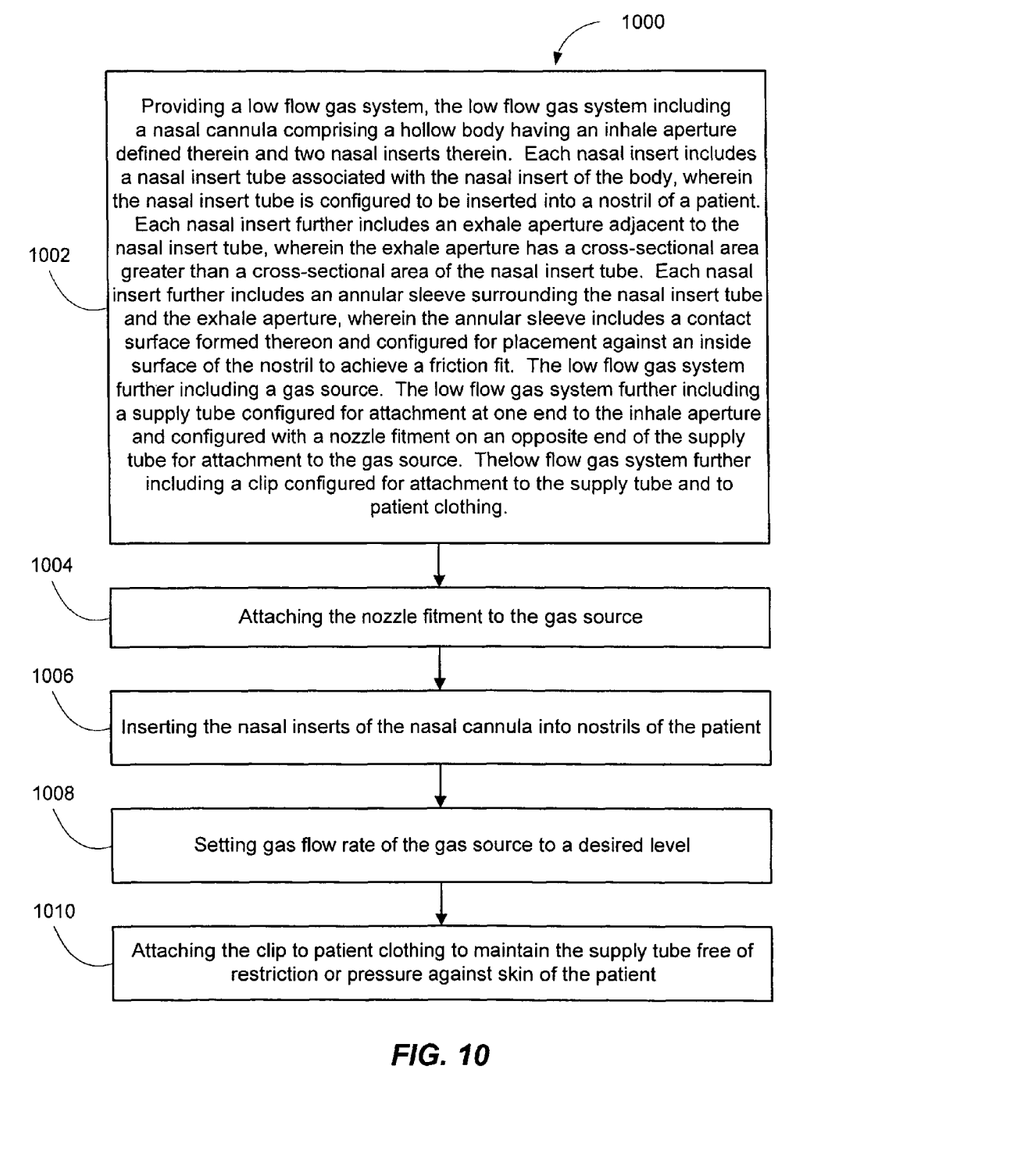
FIG. 10 is a flow chart of an embodiment of a method for delivering a low flow therapeutic gas to a patient.

FIG. 10 is a flow chart of an embodiment of a method 1000 for delivering a low flow therapeutic gas to a patient. Method 1000 may include providing a low flow gas system 1002, the low flow gas system may include a nasal cannula such as 100, 200 or 600 disclosed herein, with the nasal cannula including a nasal insert such as 250, 650, 850 or 950 as disclosed herein. Providing a low flow gas system 1002 may further include providing a gas source, a supply tube configured for attachment at one end to an inhale aperture and configured with a nozzle fitment on an opposite end of the supply tube for attachment to the gas source and a clip configured for attachment to the supply tube and to patient clothing. Method 1000 may further include attaching the nozzle fitment to the gas source 1004.

Method 1000 may further include inserting the nasal inserts of the nasal cannula into nostrils of the patient 1006. Inserting the nasal inserts 1006 may further include compressing an annular sleeve of memory foam, inserting the compressed annular sleeve into the nostrils of the patient and allowing the annular sleeve to expand within the nostrils. Method 1000 may further include setting gas flow rate of the gas source to a desired level 1008. Method 1000 may further include attaching the clip to patient clothing 1010 to maintain the supply tube free of restriction or pressure against the skin of the patient.

While the foregoing advantages of the present invention are manifested in the detailed description and illustrated embodiments of the invention, a variety of changes can be made to the configuration, design and construction of the invention to achieve those advantages. Hence, reference herein to specific details of the structure and function of the present invention is by way of example only and not by way of limitation.

What is claimed is:

1. A nasal cannula, comprising:
 a hollow body, comprising:
  a chamber;
  an intake port leading to the chamber, the intake port configured for connection to a pressurized therapeutic gas line for receiving therapeutic gas for delivery into the chamber inside the hollow body; and
  two exit ports, each exit port in fluid communication with the intake port and the chamber and configured for delivering the therapeutic gas to a patient; and
 two nasal inserts, each nasal insert connected to one of the two exit ports and configured for placement within a nostril of a patient, each nasal insert further comprising:
  a nasal insert tube connected to one of the exit ports, the nasal insert tube configured to be inserted into a nostril of a patient for delivering the therapeutic gas;
  only one exhale aperture adjacent to, but not surrounding, the nasal insert tube, the exhale aperture comprising a cross-sectional area greater than a cross-sectional area of the nasal insert tube; and
  an annular sleeve surrounding the nasal insert tube and the exhale aperture, the annular sleeve comprising an external contact surface formed thereon having a distal end opposite the hollow body, the distal end having tear drop cross-section, the external contact surface configured for placement against an inside surface of the nostril to achieve a friction fit.

2. The nasal cannula according to claim 1, wherein the nasal cannula comprises silicone.

3. The nasal cannula according to claim 1, wherein the annular sleeve comprises silicone.

4. The nasal cannula according to claim 1, wherein the annular sleeve comprises a resilient elastomer material.

5. The nasal cannula according to claim 1, wherein each of the annular sleeves forms a tear drop cross-sectioned, dual-lumen ring configured for placement entirely with the nostril.

6. The nasal cannula according to claim 1, wherein an axis of the nasal insert tube does not fall within a cross-sectional area of the exhale aperture.

7. The nasal cannula according to claim 1, further comprising a supply tube configured for attachment to, and in fluid communication with, the intake port.

8. The nasal cannula according to claim 7, further comprising a supply nozzle fitment on one end of the supply tube.

9. The nasal cannula according to claim 7, further comprising a clip configured for attachment to the supply tube and to patient clothing.

10. The nasal cannula according to claim 1, wherein the contact surface of the annular sleeve forms an exclusive contact interface with the nostril.

11. A low flow gas system, comprising:
 a nasal cannula, comprising:
  a hollow body, comprising:
   a chamber;
   an intake port leading to the chamber, the intake port configured for connection to a pressurized therapeutic gas line for receiving therapeutic gas for delivery into the chamber inside the hollow body; and
   two exit ports, each exit port in fluid communication with the intake port and the chamber and configured for delivering the therapeutic gas to a patient; and two nasal inserts, each nasal insert connected to one of the two exit ports and configured for placement within a nostril of a patient, each nasal insert further comprising:
- a nasal insert tube connected to one of the exit ports, the nasal insert tube configured to be inserted into a nostril of a patient for delivering the therapeutic gas;
- only one exhale aperture adjacent to, but not surrounding, the nasal insert tube, the exhale aperture comprising a cross-sectional area greater than a cross-sectional area of the nasal insert tube; and
- an annular sleeve having a tear drop cross-section along an outer periphery opposite the hollow body and surrounding the nasal insert tube and the exhale aperture, the annular sleeve comprising a contact surface formed thereon and configured for placement against an inside surface of the nostril to achieve a friction fit; and a supply tube configured for attachment at one end to the inhale aperture and further configured with a nozzle fitment on an opposite end of the supply tube for attachment to a gas source.

12. The system according to claim 11, further comprising a clip configured for attachment to the supply tube and to patient clothing.

13. The system according to claim 11, further comprising the gas source.

14. The system according to claim 13, wherein the gas source is an oxygen canister.

15. The system according to claim 11, wherein the annular sleeve comprises silicone.

16. An integral nasal cannula, comprising:
a hollow body having at least one intake port and two exit ports disposed therein;
two nasal inserts disposed around the two exit ports, each nasal insert further comprising:
- a nasal insert tube comprising a proximate end in fluid communication with one of the two exit ports and a distal end configured to be inserted into a nostril of a patient for delivering a therapeutic gas;
- only one exhale aperture adjacent to, but not surrounding, the nasal insert tube, the exhale aperture having a cross-sectional area greater than a cross-sectional area of the nasal insert tube; and
- an annular sleeve having an external contact surface with tear drop cross-section along an outer periphery opposite the hollow body the annular sleeve surrounding both the distal end of the nasal insert tube and the exhale aperture, the external contact surface configured for placement against an inside surface of the nostril to achieve a friction fit.

17. The integral nasal cannula according to claim 16, wherein the integral nasal cannula comprises silicone.

18. The integral nasal cannula according to claim 16, wherein the annular sleeve comprises a resilient elastomer material.

19. The nasal integral cannula according to claim 16, wherein each of the annular sleeves forms a tear drop cross-sectioned, dual-lumen ring configured for placement entirely within the nostril.

20. The integral nasal cannula according to claim 16, wherein an axis of the nasal insert tube does not fall within a cross-sectional area of the exhale aperture.

21. The integral nasal cannula according to claim 16, further comprising a supply tube configured for attachment to, and in fluid communication with, the intake port.

* * * * *